US00PP27563P3

(12) United States Plant Patent
Vlielander

(10) Patent No.: US PP27,563 P3
(45) Date of Patent: Jan. 17, 2017

(54) ***KALANCHOE* PLANT NAMED 'FIKALSAJA'**

(50) Latin Name: *Kalanchoe blossfeldiana*
Varietal Denomination: Fikalsaja

(71) Applicant: Ike J. Vlielander, De Lier (NL)

(72) Inventor: Ike J. Vlielander, De Lier (NL)

(73) Assignee: Fides B.V., De Lier (NL)

( * ) Notice: Subject to any disclaimer, the term of this patent is extended or adjusted under 35 U.S.C. 154(b) by 43 days.

(21) Appl. No.: 14/545,482

(22) Filed: May 12, 2015

(65) Prior Publication Data

US 2016/0353644 P1 Dec. 1, 2016

(51) Int. Cl.
*A01H 5/02* (2006.01)

(52) U.S. Cl.
USPC ..... Plt./338

(58) Field of Classification Search
USPC ..... Plt./338
See application file for complete search history.

*Primary Examiner* — Anne Grunberg
(74) *Attorney, Agent, or Firm* — C. A. Whealy

(57) ABSTRACT

A new and distinct cultivar of *Kalanchoe* plant named 'Fikalsaja', characterized by its compact, upright and uniformly mounded plant habit; moderately vigorous growth habit; freely branching plant habit; glossy dark green-colored leaves; uniform, early and freely flowering habit; clear yellow-colored flowers; and excellent postproduction longevity.

1 Drawing Sheet

Botanical designation: *Kalanchoe blossfeldiana.*
Cultivar denomination: 'FIKALSAJA'.

CROSS-REFERENCED TO CLOSELY RELATED APPLICATIONS

Title: *Kalanchoe* Plant Named 'Fikalcoto'
Applicant: Ike J. Vlielander
Filed: Concurrently with this application having application Ser. No. 14/545,483

BACKGROUND OF THE INVENTION

The present invention relates to a new and distinct *Kalanchoe* plant, botanically known as *Kalanchoe blossfeldiana* and hereinafter referred to by the name 'Fikalsaja'.

The new *Kalanchoe* is a product of a planned breeding program conducted by the Inventor in De Lier, The Netherlands. The objective of the breeding program is to create new freely-branching and freely-flowering *Kalanchoe* plants with attractive leaf and flower coloration.

The new *Kalanchoe* plant originated from a cross-pollination made by the Inventor in De Lier, The Netherlands in 2010 of *Kalanchoe blossfeldiana* 'Forever Midi Yellow', not patented, as the female, or seed, parent with *Kalanchoe blossfeldiana* 'Goldstrike', disclosed in U.S. Plant Pat. No. 6,632, as the male, or pollen, parent. The new *Kalanchoe* plant was discovered and selected by the Inventor as a single flowering plant from within the progeny of the stated cross-pollination in a controlled environment in De Lier, The Netherlands.

Asexual reproduction of the new *Kalanchoe* plant by vegetative terminal cuttings in a controlled environment in De Lier, The Netherlands since 2013 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Fikalsaja'. These characteristics in combination distinguish 'Fikalsaja' as a new and distinct *Kalanchoe* plant:

1. Compact, upright and uniformly mounded plant habit.
2. Moderately vigorous growth habit.
3. Freely branching plant habit.
4. Glossy dark green-colored leaves.
5. Uniform, early and freely flowering habit.
6. Clear yellow-colored flowers.
7. Excellent postproduction longevity.

Plants of the new *Kalanchoe* can be compared to plants of the female parent, 'Forever Midi Yellow'. Plants of the new *Kalanchoe* differ from plants of 'Forever Midi Yellow' in the following characteristics:

1. Plants of the new *Kalanchoe* are not as vigorous as plants of 'Forever Midi Yellow'.
2. Plants of the new *Kalanchoe* have smaller leaves than plants of 'Forever Midi Yellow'.
3. Plants of the new *Kalanchoe* have larger flowers than plants of 'Forever Midi Yellow'.
4. Plants of the new *Kalanchoe* flower earlier than plants of 'Forever Midi Yellow'.
5. Plants of the new *Kalanchoe* and 'Forever Midi Yellow' differ in flower color as plants of 'Forever Midi Yellow' have orangish yellow-colored flowers.

Plants of the new *Kalanchoe* can be compared to plants of the male parent, 'Goldstrike'. Plants of the new *Kalanchoe* differ from plants of 'Goldstrike' in the following characteristics:

1. Plants of the new *Kalanchoe* are more vigorous than plants of 'Goldstrike'.
2. Plants of the new *Kalanchoe* are more freely branching than plants of 'Goldstrike'.

3. Plants of the new *Kalanchoe* have larger flowers than plants of 'Goldstrike'.
4. Plants of the new *Kalanchoe* flower earlier than plants of 'Goldstrike'.
5. Plants of the new *Kalanchoe* and 'Goldstrike' differ in flower color as plants of 'Goldstrike' have orangish yellow-colored flowers.

Plants of the new *Kalanchoe* can be compared to plants of the *Kalanchoe blossfeldiana* 'Fikalcoto', disclosed in a U.S. Plant Patent application filed concurrently having application Ser. No. 14/545,483. In side-by-side comparisons conducted in De Lier, The Netherlands, plants of the new *Kalanchoe* differed from plants of 'Fikalcoto' in the following characteristics:

1. Plants of the new *Kalanchoe* were smaller and more compact than plants of 'Fikalcoto'.
2. Plants of the new *Kalanchoe* had lighter green-colored stems than plants of 'Fikalcoto'.
3. Plants of the new *Kalanchoe* had larger leaves than plants of 'Fikalcoto'.

BRIEF DESCRIPTION OF THE PHOTOGRAPH

The accompanying colored photograph illustrates the overall appearance of the new *Kalanchoe* plant showing the colors as true as it is reasonably possible to obtain in colored reproductions of this type. Colors in the photograph may differ slightly from the color values cited in the detailed botanical description which accurately describe the colors of the new *Kalanchoe* plant.

The photograph is a side perspective view of a typical flowering plant of 'Fikalsaja' grown in a container.

DETAILED BOTANICAL DESCRIPTION

The aforementioned photograph and following observations, measurements and values describe plants grown during the winter in 10-cm containers in a glass-covered greenhouse in De Lier, The Netherlands and under cultural practices typical of commercial *Kalanchoe* production. During the production of the plants, day and night temperatures ranged from 19° C. to 20° C. and light levels ranged from 10,000 lux to 50,000 lux. Plants received long day/short night conditions (more than 14 hours of light) for about three weeks then plants received photoinductive short day/long night conditions (minimum 14 hours darkness) until flowering. Plants were 15 weeks old when the photograph and description were taken. In the detailed description, color references are made to The Royal Horticultural Society Colour Chart, 2007 Edition, except where general terms of ordinary dictionary significance are used.

Botanical classification: *Kalanchoe blossfeldiana* 'Fikalsaja'.

Parentage:

*Female, or seed, parent.*—*Kalanchoe blossfeldiana* 'Forever Midi Yellow', not patented.

*Male or pollen parent.*—*Kalanchoe blossfeldiana* 'Goldstrike', disclosed in U.S. Plant Pat. No. 6,632.

Propagation:

*Type.*—By vegetative terminal cuttings.

*Time to initiate roots, summer.*—About ten days at temperatures about 21° C.

*Time to initiate roots, winter.*—About two weeks at temperatures about 21° C.

*Time to produce a rooted young plant, summer.*—About 20 days at temperatures about 21° C.

*Time to produce a rooted young plant, winter.*—About 27 days at temperatures about 21° C.

*Root description.*—Fine, fibrous; greyish white in color.

*Rooting habit.*—Freely branching; dense.

Plant description:

*Plant and growth habit.*—Compact, upright and uniformly mounded plant habit; freely flowering habit with numerous cymes positioned above the foliar plane; inverted triangle with rounded crown; appropriate for 7.5 to 15.25-cm containers; moderately vigorous growth habit.

*Plant height at flowering.*—About 15 cm.

*Plant diameter at flowering.*—About 15 cm.

*Branching habit.*—Freely branching habit with usually about five to seven lateral branches developing per plant; pinching (removal of the terminal apex) is not required but will enhance lateral branch development.

Lateral branch description:

*Length.*—About 11 cm to 16 cm.

*Diameter.*—About 2 mm to 5 mm.

*Internode length.*—About 2 cm to 3 cm.

*Aspect.*—Erect.

*Strength.*—Moderately strong.

*Texture.*—Smooth, glabrous.

*Color.*—Close to 137D.

Leaf description:

*Arrangement.*—Opposite, simple; generally symmetrical.

*Quantity per plant.*—About six to ten mature leaves and about ten to 14 generative leaves.

*Length.*—About 10 cm.

*Width.*—About 7 cm.

*Shape.*—Ovate to elliptic.

*Apex.*—Obtuse.

*Base.*—Acute.

*Margin.*—Crenate.

*Texture, upper and lower surfaces.*—Smooth, glabrous; coriaceous; succulent; glossy.

*Venation pattern.*—Pinnate.

*Color.*—Developing and fully developed leaves, upper surface: Close to N137A; venation, close to N137A to N137B. Developing and fully developed leaves, lower surface: Close to 147B; venation, close to 147B.

*Petioles.*—Length: About 1.5 cm. Diameter: About 4 mm to 8 mm. Texture, upper and lower surfaces: Smooth, glabrous; coriaceous; succulent. Color, upper and lower surfaces: Close to N137A to N137B.

Flower description:

*Flower arrangement and habit.*—Single flowers arranged singly in axillary cymes; uniform and freely flowering habit with usually more than 25 open flowers and more than 25 flower buds per lateral branch and more than 150 open flowers and flower buds developing per plant; plants flower continuously for at least six weeks.

*Fragrance.*—None detected.

*Natural flowering season.*—Plants of the new *Kalanchoe* initiate and develop flowers under short day/long night conditions or during November and December in The Netherlands; flower initiation and development can also be induced under artificial short day/long conditions (at least 14 hours of darkness).

*Time to flower*.—Early flowering habit, under short day/long night photoinductive conditions, plants begin flowering about eight to ten weeks; actual time to flower is primarily dependent upon temperature and light intensity.

*Post-production longevity*.—Excellent post-production longevity; plants maintain good foliage and flower substance for about 46 days under interior conditions; individual flowers last about 16 days on the plant; flowers persistent.

*Flower diameter*.—About 1.9 cm.

*Flower length* (*height*).—About 1.4 cm.

*Flower buds*.—Length: About 1.4 cm. Diameter: About 3 mm. Shape: Initially oblong, becoming tubular ovoid with development. Color: Close to 138C and becoming closer to 12C with development.

*Petals*.—Arrangement: Four in a single whorl. Length: About 7 mm. Width: About 6 mm. Aspect: Flat to somewhat upright. Shape: Ovate. Apex: Acute. Base: Obtuse. Margin: Entire. Texture, upper and lower surfaces: Smooth, glabrous. Color: When opening, upper surface: Close to 12A. When opening, lower surface: Close to 12C to 12D. Fully opened, upper surface: Close to 12A to 12B; color becoming closer to 12C with development. Fully opened, lower surface: Close to 12D.

*Sepals*.—Appearance: Four in a single whorl. Length: About 9 mm. Width: About 2 mm. Shape: Oblong, pointed. Apex: Acute. Base: Obtuse. Margin: Entire. Aspect: Upright, rigid. Texture, upper and lower surfaces: Smooth; glabrous. Color, upper and lower surfaces: Close to 138B.

*Peduncles*.—Length: About 4 mm. Diameter: About 1 mm. Aspect: Erect, rigid. Strength: Strong. Texture: Smooth, glabrous. Color: Close to 138B.

*Reproductive organs*.—Androecium: Stamen number: About eight per flower. Anther shape: Elliptic, flat. Anther length: About 0.3 mm. Anther color: Close to 150D. Amount of pollen: Scarce. Pollen color: Close to 12A. Gynoecium: Pistil number: About four. Pistil length: About 1 mm. Style length: About 1 mm. Style color: Close to 138D. Stigma shape: Flat. Stigma color: Close to 8D. Ovary color: Close to 138D.

*Seeds*.—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen & pest resistance: Plants of the new *Kalanchoe* have not been observed to be resistant to pests and pathogens common to *Kalanchoe* plants.

It is claimed:

1. A new and distinct *Kalanchoe* plant named 'Fikalsaja' as illustrated and described.

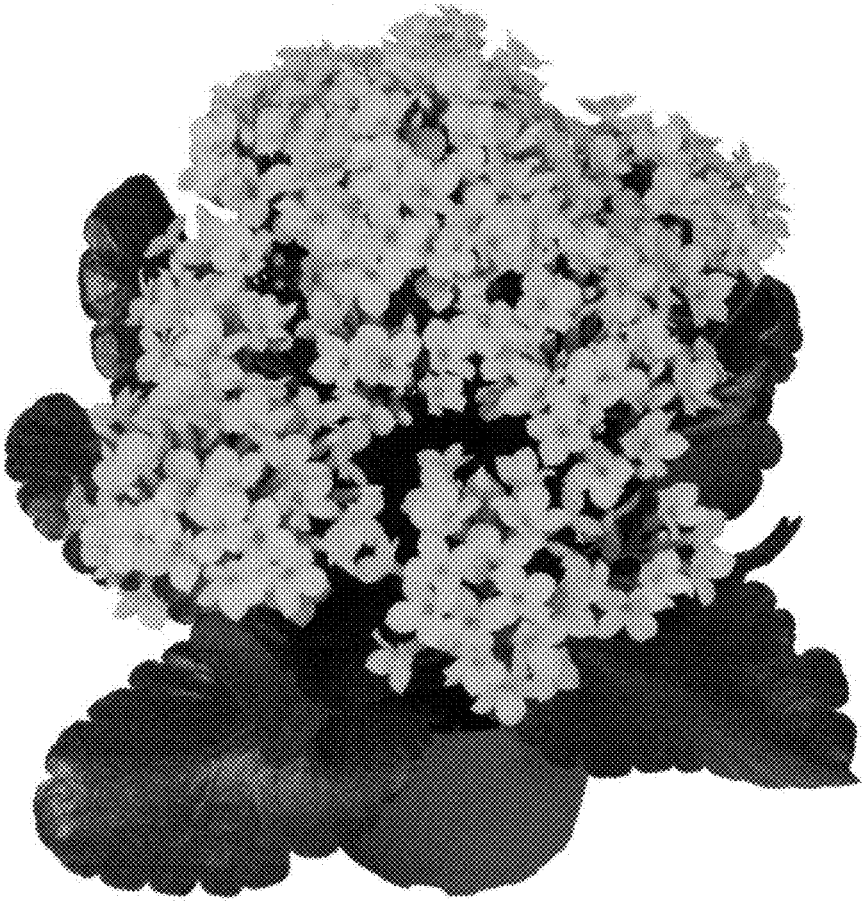

* * * * *